United States Patent [19]

Hiejima

[11] Patent Number: 5,514,096
[45] Date of Patent: May 7, 1996

[54] APPARATUS AND BALLOON FOR DOSING A LIQUID MEDICINE

[75] Inventor: Katsuhiro Hiejima, Ootsu, Japan

[73] Assignee: Nissho Corporation, Osaka, Japan

[21] Appl. No.: 350,469

[22] Filed: Dec. 7, 1994

[30] Foreign Application Priority Data

Dec. 28, 1993 [JP] Japan ................... 5-353242

[51] Int. Cl.⁶ ........................................ A61M 37/00
[52] U.S. Cl. ............................... 604/132; 604/153
[58] Field of Search ................... 604/96, 97, 101, 604/131, 132, 133, 183, 185, 212, 214, 151, 153

[56] References Cited

U.S. PATENT DOCUMENTS

| 3,895,631 | 7/1975 | Buckles et al. . | |
|---|---|---|---|
| 3,993,069 | 11/1976 | Buckles et al. . | |
| 4,140,117 | 2/1979 | Buckles et al. . | |
| 4,201,207 | 5/1980 | Buckles et al. . | |
| 4,386,929 | 6/1983 | Peery et al. . | |
| 4,909,790 | 3/1990 | Tsujikawa et al. . | |
| 4,915,693 | 4/1990 | Hessel . | |
| 4,938,751 | 7/1990 | Leeper et al. . | |
| 4,964,853 | 10/1990 | Sugiyama et al. | 604/96 |
| 5,011,477 | 4/1991 | Winchell et al. . | |
| 5,061,243 | 10/1991 | Winchell et al. | 604/132 |
| 5,080,652 | 1/1992 | Sancoff et al. . | |
| 5,201,706 | 4/1993 | Noguchi et al. | 604/96 |
| 5,290,306 | 3/1994 | Trotta et al. | 604/194 |
| 5,328,477 | 7/1994 | Sitko | 604/134 |
| 5,344,401 | 9/1994 | Radisch et al. | 604/96 |

FOREIGN PATENT DOCUMENTS

| 0452912A2 | 10/1991 | European Pat. Off. . |
| 3-140163 | 6/1991 | Japan . |
| 5-115542 | 5/1993 | Japan . |
| WO 93/14797 | 8/1993 | WIPO . |

*Primary Examiner*—C. Fred Rosenbaum
*Assistant Examiner*—N. Kent Gring
*Attorney, Agent, or Firm*—Ronald J. Kubovcik

[57] ABSTRACT

An apparatus for dosing a liquid medicine. The apparatus includes a balloon having openings through which the medicine is charged and discharged; a housing holding the balloon and having an outlet adjacent to one of the openings; and a delivery assembly extending from the outlet. The balloon is composed of an inner layer, an outer layer covering the inner layer and an impermeable membrane interposed between the inner and outer layers. The inner layer is made of a chemically resistant resin not reactive with the medicine, the outer layer is made of an elastic rubber more contractive than the inner layer when the balloon is inflated with the medicine, and the impermeable membrane prevents any additives in the elastic rubber from migrating into the medicine, even if the additives were not previously removed. The balloon can be manufactured in a shorter time than a conventional balloon and will not cause an allergic reaction or anaphylactic shock inherent in untreated elastic rubbers.

10 Claims, 2 Drawing Sheets

APPARATUS AND BALLOON FOR DOSING A LIQUID MEDICINE

BACKGROUND OF THE INVENTION

1. Field of the Invention

The present invention relates to an apparatus for continuously dosing a patient with a liquid medicine at a moderate rate, by feeding it into a vein, urinary balloon or like organ of the patient. More particularly, the present invention relates to an apparatus that comprises a balloon accommodating an amount of liquid medicine to be supplied to the patient at a constant and moderate rate and in a continuous manner.

2. Description of Prior Art

A device of a certain type for continuously dosing a patient with an antibiotic, anti-cancer medicine or the like is disclosed in Japanese Unexamined Patent Publication Sho. 50-108790. This device comprises an elastic balloon which accommodates the medicine and tends to shrink to force it into the patient's body. A bladder for a liquid medicine dispenser is proposed in Japanese Patent Publication Sho. 63-51702. The bladder or balloon is made of a synthetic polyisoprene from which harmful additives are previously removed. A harmless antioxidant which is substantially insoluble in blood is blended with such a purified polyisoprene.

The present inventor proposed a few years ago an improved balloon also for use in a device to continuously and constantly exert pressure on a liquid medicine. This balloon is a length of natural rubber tube having its inner surface coated with a silicone resin membrane, and is of a composite structure in cross-section as shown in Japanese Unexamined Patent Publication Hei. 4-2360. The present inventor had intended that the silicone membrane would effectively prevent the migration of any additives in the natural rubber into the medicine.

Contrary to the present inventor's expectation, migration of natural rubber additives has been observed in liquid medicines one or more days after being filled into the balloon. Therefore, such usual additives have had to be initially removed from the natural rubber, before blending the natural rubber with an adequate amount of an antioxidant that is harmless and insoluble in blood, as disclosed in the Japanese Unexamined Patent Publication Hei. 5-115542.

However, such an intricate treatment of the rubber to remove usual additives and then to blend the rubber with an antioxidant takes a long time. Further, there is a likelihood that the quality of the treated rubber will undesirably vary depending on the conditions of treatment.

The present inventor has searched for a novel material for a balloon that would be composed primarily of an elastic rubber not previously treated (unlike the natural rubbers), but in which additives would nevertheless be inhibited from migrating into a liquid medicine.

SUMMARY OF THE INVENTION

An object of the present invention is to provide a novel apparatus for dosing a liquid medicine. This object is accomplished according to the present invention by an apparatus comprising: a balloon having openings and being adapted to receive an amount of a liquid medicine through one of the openings so as to subsequently deliver it through the other opening; a housing holding the balloon and having an outlet adjacent to this other opening; and a delivery assembly extending from the outlet and regulating the flow of the medicine effluent from the balloon. The balloon is composed of an inner layer serving as an inner wall of the balloon, an outer layer disposed outside the inner layer and an impermeable membrane interposed between the inner and outer layers. The inner layer is made of a chemically resistant resin that is inactive to the medicine. The outer layer is made of an elastic rubber more elastic than the inner layer when the balloon is inflated with the medicine. The impermeable membrane prevents any additives in the elastic rubber from migrating into the medicine.

In the most preferable mode of the invention, the balloon further comprises a liquid lubricant layer between the outer layer and the impermeable membrane.

The impermeable membrane can be formed of at least one thermoplastic resin selected from the group consisting of polyvinylidene chloride resins, polyvinyl chloride resins, polyamides, thermoplastic polyesters, and ethylene-vinyl acetate copolymers.

The delivery assembly can comprise a flow regulator to control the flow rate of the liquid medicine.

In operation, the balloon will be inflated with an appropriate amount of the medicine so that subsequent contraction of the balloon will force the medicine into a patient's body. As described above, the balloon is made of a composite material comprising a chemically resistant inner layer and an outer elastic rubber layer containing additives, wherein an impermeable membrane present between the layers intercepts the additives and prevents the additives from diffusing into the inner layer. Any additives enhancing durability of the elastic rubber are prevented from migrating into the chemically resistant inner layer and from consequently contaminating the liquid medicine in the balloon. Thus, a patient will be protected from allergic reaction and anaphylactic shock which could otherwise be caused by the elastic rubber. In a case wherein a lubricant layer intervenes between the outer layer and the impermeable membrane, there is no possibility that a gap is produced locally between the inner and outer layers when the inner layer is inflated following the outer layer which is of a higher expansion stress. An undesired variation in flow rate of the medicine will not take place in the course of time at the outlet of the balloon, because any change in pressure will not occur at the inlet of the flow regulator. Such a synchronous and smooth shrinkage of the layers ensures a constant and stable delivery of the liquid medicine to the patient.

BRIEF DESCRIPTION OF THE DRAWINGS

In the drawings showing some embodiments of the present invention.

PREFERRED EMBODIMENTS

Figure 1:
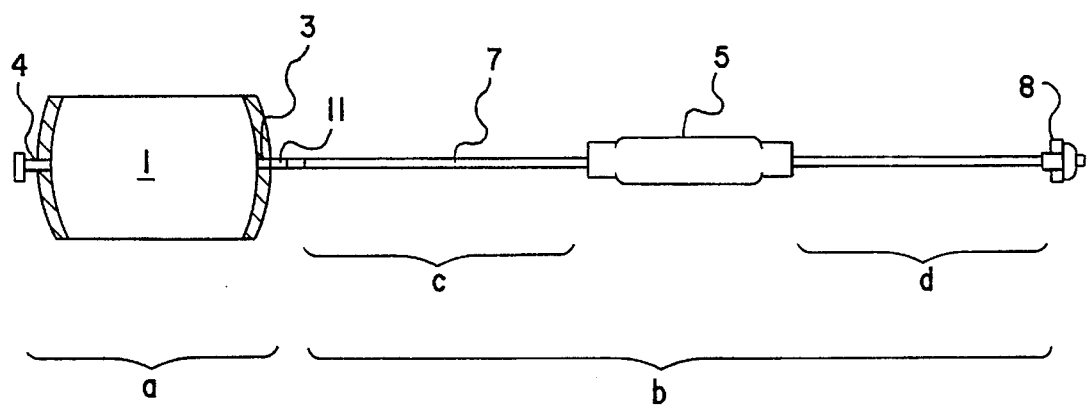
FIG. 1 is a schematic view of an apparatus for dosing a liquid medicine according to the present invention, wherein the apparatus is provided in accordance with a first embodiment and is formed as a dosing set comprising a balloon.

An embodiment of the present invention will now be described referring to the drawings, in which the reference symbol 'a' denotes a balloon assembly and the symbol 'b' denotes a tube line as the delivery assembly for discharging a liquid medicine from the balloon assembly. The reference numerals 1–9, 11 and 12, respectively, denote in this order: a balloon (1); a housing (2); an outlet (3) for the medicine; an inlet (4) therefor; a flow regulator (5); a breakable closure (6); a tubular passage (7); a connector (8); a spring (9); a stopper (11) (comprising, for example, a breakable closure); and a press plate (12). The numerals 25–27 denote an inner layer, a middle layer and an outer layer, respectively.

Figure 2:
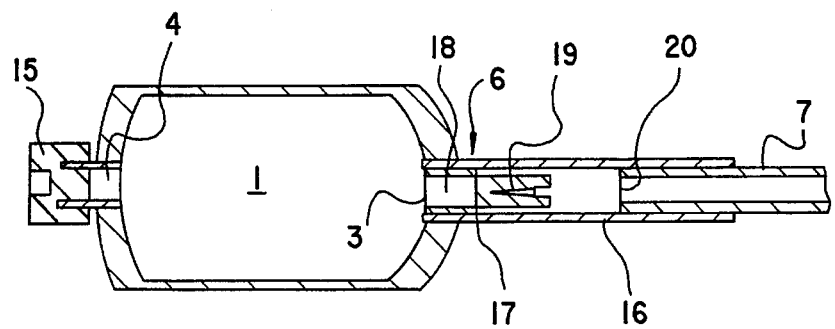
FIG. 2 is a cross section of the balloon employed in a balloon assembly and filled with the liquid medicine.

The dosing set provided in the first embodiment and shown in FIG. 1 is an apparatus for dosing a liquid medicine, and comprises a balloon assembly 'a' and a tube line 'b' as the delivery assembly. The balloon assembly 'a' in turn comprises a balloon 1 which remains somewhat depressed even after being filled and inflated with the liquid medicine, as shown in FIG. 2. The outlet 3 and the inlet 4 for the liquid medicine are formed in opposite walls of the balloon. An elastic plug 15 made of a rubber or the like fits in the inlet 4. A needle of a syringe containing the liquid medicine can pierce the plug and supply the balloon with a required amount of the medicine. The plug may be made of a synthetic rubber such as silicone rubber, butyl rubber or any natural rubber, because these rubbers are not readily broken by a needle and can prevent leakage of the compressed liquid medicine. A balloon having a cylindrical shape with its top or bottom closed, or of a spherical shape, can be employed in place of one having flat side walls as shown in FIGS. 1 and 2. The cylindrical balloon can be expandable both in radial and longitudinal directions. The size and wall thickness of the balloon are variable depending on the volume and feed time of the medicine.

Outlet 3 is preferably located opposite to inlet 4. The outlet and inlet formed in sides of the bag-shaped balloon facing one another are lengths of a flexible tube 16. Each length of the tube is liquid-tightly heat sealed to an aperture for securing the outlet or inlet. A breakable closure 6 disposed in the outlet tube 16 has a readily breakable weak point 17, and operates to inhibit the liquid medicine from unintentionally flowing out of the balloon 1 into the tubular passage 7. In the embodiment shown in FIG. 2, the breakable closure 6 comprises a cylindrical portion 18, weak point 17 and a columnar portion 19 which are arranged in this order. The outer diameter of the columnar portion 19 having at least two longitudinal grooves is smaller than the inner diameter of the outlet tube 16. The medicine can thus flow through an annular gap present between the outer periphery of the columnar portion 19 and the inner periphery of the flexible tube 16. Before start of the dosing operation, the cylindrical portion 18 is filled with the liquid medicine in the balloon. The columnar portion 19 closing the cylindrical portion 18 does, however, stop a further forward flow of the liquid medicine. In order to start the dosing, the breakable closure 6 will be bent at its weak point 17 manually from the outside of the tube 16, so as to tear the columnar portion 19 off the cylindrical portion 18. The thus freed columnar portion will move forward and be stopped by a proximal end 20 of the tubular passage 7 inserted in the outlet tube 16. The two or more longitudinal grooves formed in the outer surface of columnar portion 19 extend from its middle region towards its distal end, whereby the liquid medicine can freely flow along the outer periphery into the tubular passage 7. Although the outlet 3 and inlet 4 are located opposite to each other in FIGS. 1 and 2, they may alternatively be formed at the same region of the bag-shaped balloon in a manner disclosed in Japanese Unexamined Patent Publication No. 2-11160.

Figure 4:
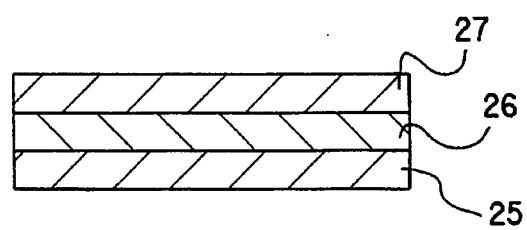
FIG. 4 is an enlarged cross section of a part of the balloon in the first embodiment.

The balloon 1 is a multi-layered composite structure in cross-section as shown in FIG. 4. The inner layer 25 is made of a chemically resistant resin, the outer layer 27 is made of an elastic rubber containing various additives. The impermeable membrane serving as a middle layer 26 sandwiched between the inner and outer layers almost perfectly prevents the additives from migrating into the inner layer. The elastic material of the outer layer 27 may be selected from an elastomer or a natural rubber such a silicone rubber, butyl rubber, acrylonitrile-butadiene rubber, butadiene rubber, isoprene rubber, polyurethane rubber, styrene-butadiene rubber, Perprene (an elastic polyester made by Toyobo Co.), Clayton rubber (a block copolymer of polystyrene made by Shell Oil Co.) and the like; a mixture thereof; and a laminated sheet composed of these rubbers. The various additives blended with the elastic material include a stabilizer for improving its durability; an antioxidant for retarding oxidation or ozonolysis; a reinforcing agent; a plasticizer or softener for improving the processability of the material; and reactants such as a vulcanizer, a vulcanization accelerator or assistant.

Figure 5:
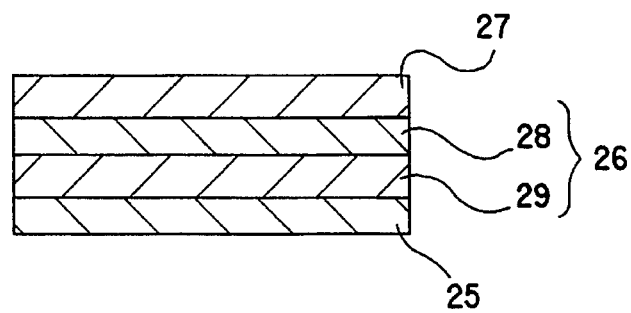
FIG. 5 is an enlarged partial cross section of the balloon provided in a second embodiment.

The chemically resistant resin for the inner layer 25 must have a lower contraction stress than the outer layer 27, when the balloon is filled with the liquid medicine. Elastic rubbers and thermoplastic resins from which the inner layer material is selected should neither be reactive with the liquid medicine nor contain any additives soluble therein. For example, the inner layer can be a film, a sheet or a coating composed of a thermoplastic resin such as polyethylene, polypropylene, polyvinyl chloride, polyester, polyamide, polycarbonate or polystyrene. The material for forming the impermeable membrane has a permeability which is less than 20 ml•mm/m$^2$•24hrs•atm. This impermeable membrane as described above, is situated between the layers and is effective to prevent the additives in the outer layer from migrating into the inner one. It can be a single film, a laminated film or a coating made of a polyvinylidene chloride; a copolymer of vinylidene chloride; a polyvinyl chloride; a copolymer of vinyl chloride; a polyamide such as nylon 6, nylon 66 and polymetaxylylene adipamide; a thermoplastic polyester such as polyethylene terephthalate or a copolymer thereof; an ethylene-vinyl acetate copolymer; a polyacrylonitrile; a polyvinyl alcohol; or like resin. FIG. 5 illustrates a second embodiment which provides a modified cross-sectional structure of the balloon such that the middle layer 26 is composed of an impermeable membrane 29 and a liquid lubricant layer 28.

The lubricant layer 28 prevents a local gap from forming between the outer and inner layers when the balloon 1 expands or shrinks. The liquid lubricant can be a silicone oil, a polyglycol, a liquid hydrocarbon, a polyphenyl ether, a grease or the like. The lubricant layer must be at least 0.01 μm thick, because a layer thinner than 0.01 μm is insufficient to avoid the formation of a local gap. In a case wherein the impermeable membrane 29 is composed of laminated elemental membranes of chemically resistant resins, the lubricant layer 28 is interposed between the outer layer 27 and the elemental membrane facing it.

In order to manufacture the balloon 1, a cylindrical material (inner balloon) can be folded in a longitudinal direction, and a liquid lubricant will be applied to the outer surface adjacent to a closed end of the cylindrical material, which will subsequently be inserted in another cylindrical material (outer balloon) having its one end closed. Alternatively, the liquid lubricant will be poured into a space present between the inner and outer balloons, before the outer one is caused to cover the outer periphery of the inner one which has been coated with impermeable membrane 29. Subsequently, compressed air will be introduced into the inner balloon through its opening, to thereby inflate the balloon 1. The compressed air will be exhausted from the inner balloon before an end portion of an appropriate length of the outer balloon is severed from its remainder and the thus severed edge is sealed.

The tube line 'b' for dosing the liquid medicine comprises outlet 3 from the balloon 1; tubular passage 7; stopper 11 disposed at the proximal end of the tubular passage; and connector 8 disposed at the distal end thereof. The tube line can further comprise flow regulator 5, if necessary. The liquid medicine effluent from the balloon 1 will flow through the tube line 7 towards the connector 8 so as to be delivered to a biopsy needle or a catheter (not shown) connected thereto, so that a patient's body receives the medicine from the needle or catheter.

The regulator 5 controlling the flow rate of the medicine can comprise for example a thin pipe having a fine inner diameter of 10–500 μm as disclosed in Japanese Unexamined Patent Publication No. 3-140163. Such a thin pipe will lower the flow rate of liquid medicine to such an extent that the injection thereof can last a considerably long time. The length of the thin pipe is for example 1 cm or more and the outer diameter thereof is 5–500 times as large as the inner diameter. In a case wherein the thin pipe 25 is longer than 30 cm, it can be coiled and accommodated in a case 26 as shown in FIG. 4 in Publication 3-140163 so as to preferably shorten the tubular passage 7. The flow regulating thin pipe can be a metal pipe, a plastic pipe or a glass pipe, as the present applicant has already proposed in Japanese Unexamined Patent Publication 2-11160 or 3-140163.

The flow regulator 5 can be disposed at any location along the tubular passage 7, but, more preferably, is located remote from the connector for convenient operation. A downstream section 'd' of the passage 7 extends between the flow regulator 5 and the connector 8, with an upstream section 'c' extending between the balloon outlet 3 and the regulator 5. The former section is smaller in inner diameter than the latter. The inner diameter of the downstream section 'd' can be 15–85%, or more desirably, 30–70% of that of the upstream section 'c'. Such a ratio will also depend on the length of the downstream section 'd'. A filter for removing fine impurities from the liquid medicine can be provided between the stopper 11 and the flow regulator 5. The filter, which is desirably located near the end of the flow regulator, can be a small mass of a textile material or a sintered material. The tubular passage 7 can be formed of a soft polyvinyl chloride resin, a polypropylene, a polyethylene or the like resin. The connector 8 at the distal end of said passage 7 is Luer-tapered to firmly fit onto a proximal end of a vein needle, a PSV set or a catheter. A check valve (not shown) can be equipped in the connector so as to prevent the liquid medicine from flowing backward due to the venous pressure.

Figure 3:
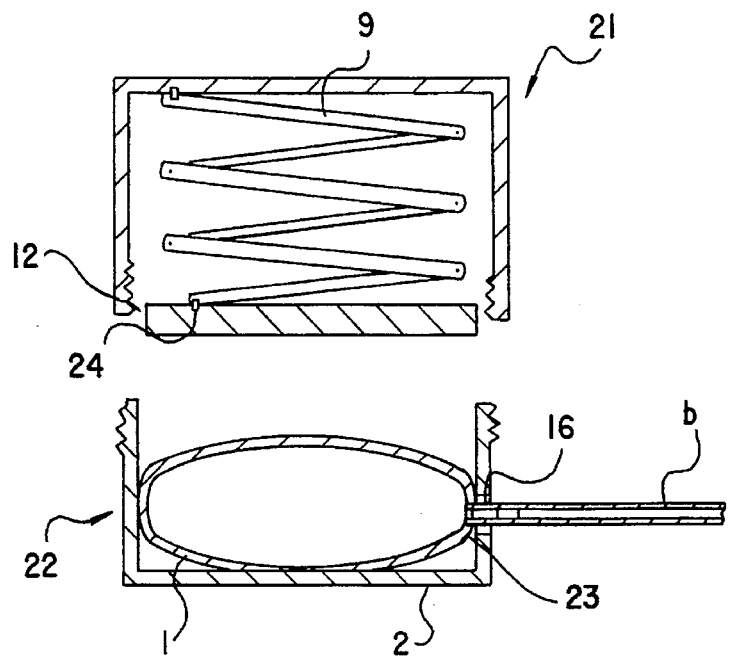
FIG. 3 is a detailed cross section of the balloon assembly constituting the dosing set.

FIG. 3 shows in cross section and in more detail the balloon assembly in the apparatus formed as the dosing set. The housing comprises a lid 21 and a container 22 which accommodates the balloon. An aperture 23 opened through a wall of the container 22 receives the flexible tube 16 such that the tube line 'b' is located outside the container 22. The lid 21 can be held fastened to the container 22 by means of a male screw thread and a female screw thread, respectively, formed around the openings of the lid and container, during the dosing of the liquid medicine. The spring 9 and the press plate 12 for pressing the balloon 1 are secured to and held in the lid 21. One end of the spring 9 is fixed by a fastener to the ceiling of the lid, with the other end of the spring being anchored to the press plate by another fastener 24.

In use of this apparatus, the balloon 1 will be charged at first with a required amount of the liquid medicine, through the inlet 4 and using an injector having a needle. After placing the balloon in the container 22, the lid 21 will be screwed onto it so that the press plate 12 is urged by the spring 9 in the lid presses the balloon. Subsequent to this preliminary operation, the breakable closure 6 will be broken at its weak point whereby the medicine flows in to the tubular passage 7. The medicine will further advance through the flow regulator 5 and the connector 8, and flow into the patient's body. Any constantly pressing or pulling spring can take the place of the coiled spring 9 shown in FIG. 3.

Although a typical example of an apparatus for dosing a liquid medicine has been described referring to FIGS. 1 to 3, the balloon as described hereinabove can be used in any of the other apparatuses disclosed in: Japanese Patent Publication No. 3-55142; Japanese Unexamined Patent Publications 50-10879; 2-11160; 3-170163 and 5-220204; Japanese Domestic Laying-Open Gazette of International Patent Applications 1-510451; and 3-505538.

EXAMPLE 1

A vulcanized natural rubber sheet 1 mm thick and a polyethylene sheet 0.15 mm thick were used to sandwich therebetween a polyvinylidene chloride sheet 0.45 mm thick. This impermeable layer has an oxygen permeability of 4.5 ml•mm/m$^2$•24hrs•atm. After laminating the sheets to provide a composite sheet, two circular samples having a diameter of 94 mm were severed from the remainder of this composite sheet. An inlet tube and an outlet tube were set in place through the facing portions of the circular samples with the polyethylene layer facing one another, and the annular edges were heat sealed to prepare a balloon having a shape as shown in FIG. 2. Then, 100 ml of distilled water was forced into the balloon through the inlet tube. This balloon containing the distilled water was held at room temperature for one week before its absorbance of light at a wavelength of 220 nm was measured. The result is described in Table 1.

EXAMPLES 2–7

Various plastic sheets as listed in Table 1 were each sandwiched between the same rubber sheet and the same polyethylene sheet as described in Example 1. Balloons were then prepared and tested with respect to their absorbance in the same manner as in Example 1, to give the results also described in Table 1.

REFERENCE 1

A vulcanized natural rubber sheet 1 mm thick was subjected to a Soxhlet extraction for 3 hours, using a mixed solvent of 1 part by volume of acetone and 2 parts by volume of hexane, so as to remove the additives in the rubber. This sheet was then immersed at 25° C. for 24 hours, in a 0.01 g/ml solution of 1,3,5-trimethyl-2,4,6-tris(3,5-di-t-butyl-4-hydroxybenzyl) benzende (hereinafter referred to as 'BHT') in the mixed solvent. The sheet was then washed with ethanol and dried at 25° C. for 12 hours. After this treatment, two circular samples having a diameter of 94 mm were severed from the remainder of the rubber sheet. An inlet tube and an outlet tube were set in place through the facing portions of the samples, and their annular edges were heat sealed to prepare a balloon having a shape as shown in FIG. 2. Then, 100 ml of distilled water was forced into the balloon through the inlet tube. This balloon containing distilled water was held at room temperature for one week, before its absorbance of light at a wavelength of 220 nm was measured. The result is described in Table 2.

REFERENCE 2

The same vulcanized natural rubber sheet 1 mm thick as used in Reference 1 was used in its untreated state. Balloons were then prepared and tested with respect to their absorbance in the same manner as in Reference 1. In detail, an inlet tube and an outlet tube were set in place through the facing portions of circular samples, and their annular edges were heat sealed to prepare a balloon having a shape as shown in FIG. 2. Then, 100 ml of distilled water was forced into the balloon through the inlet tube. This balloon containing the distilled water was held at room temperature for one week, before its absorbance of light at a wavelength of 220 nm was measured to give the results also described in Table 2.

REFERENCE 3

The same vulcanized natural rubber sheet 1 mm thick as used in Reference 2 was used in its untreated state, in combination with a polyethylene sheet 0.15 mm thick. Balloons were then prepared by arranging two circular samples to have their polyethylene layers facing one another in the same manner as described above. In detail, an inlet tube and an outlet tube were set in place through the facing portions of the samples whose polyethylene layers facing one another, and their annular edges were heat sealed to prepare a balloon having a shape as shown in FIG. 2. Then, 100 ml of distilled water was forced into the balloon through the inlet tube. This balloon containing the distilled water was held at room temperature for one week, before its absorbance of light at a wavelength of 220 nm was measured. The balloon was tested with respect to its absorbance in the same manner as in Reference 2, to give the results also described in Table 2.

REFERENCE 4

A synthesized polyisoprene rubber sheet 1 mm thick was subjected to Soxhlet extraction for 3 hours using a mixed solvent of 1 part by volume of acetone and 2 parts by volume of hexane, so as to remove the additives in the rubber. This sheet was then immersed at 25° C. for 24 hours, in a 0.01 g/ml solution of BHT in the mixed solvent. The sheet was then washed with ethanol and dried at 25° C. for 12 hours. After this treatment, two circular samples having a diameter of 94 mm were severed from the remainder of the rubber sheet. An inlet tube and an outlet tube were set in place through the facing portions of the samples, and their annular edges were heat sealed to prepare a balloon having a shape as shown in FIG. 2. Then, 100 ml of distilled water was forced into the balloon through the inlet tube. This balloon containing the distilled water was held at room temperature for one week, before its absorbance of light at a wavelength of 220 nm was measured. The result is described in Table 2.

REFERENCE 5

The same polyisoprene rubber sheet 1 mm thick as described in Reference 4 was used in its untreated state. Balloons were then prepared in the described manner. In detail an inlet tube and an outlet tube were set in place through the facing portions of circular samples. Then, their annular edges were heat sealed to prepare a balloon having a shape as shown in FIG. 2. Subsequently, 100 ml of distilled water was forced into the balloon through the inlet tube. This balloon containing the distilled water was held at room temperature for one week, before its absorbance of light at a wavelength of 220 nm was measured. The balloon was tested with respect to its absorbance in the same manner as in Reference 1, to give results also described in Table 2.

TABLE 1

| Example | Middle Layer | Oxygen Permeability $\frac{ml \cdot mm}{m^2 \cdot 24 \, hrs \cdot atm}$ | Thickness of Middle Layer mm | Absorbance |
| --- | --- | --- | --- | --- |
| 1 | polyvinylidene chloride | 4.50 | 0.45 mm | 0.0120 |
| 2 | nylon 6 | 7.50 | 0.51 mm | 0.0186 |
| 3 | polytethylene terephthalate | 5.50 | 0.43 mm | 0.0284 |
| 4 | polyvinyl chloride | 16.54 | 0.45 mm | 0.0259 |
| 5 | ethylene-vinyl acetate copolymer | 0.96 | 0.48 mm | 0.0331 |
| 6 | polyvinyl alcohol | 3.38 | 0.46 mm | 0.0408 |
| 7 | polyacrylo nitrile | 1.00 | 0.50 mm | 0.0413 |

TABLE 2

| References | 1 | 2 | 3 | 4 | 5 |
| --- | --- | --- | --- | --- | --- |
| Absorbance | 0.0442 | 0.1114 | 0.0533 | 0.0990 | 1.5930 |

As will be seen from Tables 1 and 2, the light absorbance of the distilled water held in the balloons which were made of the materials provided in Examples 1–7 was distinctively less than that for the treated natural rubber in Reference 1. Thus, it is apparent that the additives contained in the outer elastic rubber layer of the invention scarcely migrated into the distilled water.

EXAMPLE 8

A laminated tube consisting of the inner polyethylene tube as in Example 1 and an outer polyvinylidene tube was folded in a longitudinal direction. This laminated tube was then immersed in a silicone oil, as a liquid lubricant so that a silicone oil coating was formed on the outer surface of the laminated tube. The silicone oil has a viscosity is 800 cSt. at 25° C. The coated laminated tube was subsequently inserted in a vulcanized natural rubber tube as in Example 1. The silicone oil was then poured into between the laminated tube and the rubber tube. The openings of the tubes were then secured one to another, before loading the inside of the inner tube with compressed air to thereby inflate the composite tube. An excessive end of the treated natural rubber tube was then cut and removed from the remainder so that the length of this tube coincided with the polyethylene tube. The end opening of the rubber tube was sealed, and compressed air was exhausted therefrom. The silicone oil layer spread through out the space between the overlapping tubes, and its thickness was 0.09 µm. A balloon assembly 'a' prepared in this manner was filled with 60 ml of water through an inlet 4 as shown in FIG. 1, using a syringe. There was observed no clearance between the laminated tube and the rubber tube, that is, the outer surface of the former was maintained in close contact with the inner surface of the latter, while the balloon was being inflated and expanded by the water. At the next step, the breakable closure 6 was broken at its weak point so as to allow the water to flow into and through the tube line 'b'. The flow regulator was a coiled extremely thin pipe of polyvinyl chloride, wherein its outer and inner diameters and its length were: 1.00 mm, 0.10 mm and 250 mm, respectively. The balloon 1 was set in a test position, with its inlet being held up and its outlet down. A venous injector needle attached to a connector was vertically remote about 50 mm from the level of the water in the balloon, so that the water continuously dripped. The water continued to flow out of the balloon almost constantly at an average dripping rate of 2.5 ml/hr. It took about 23 hours for the balloon to become empty, and a standard deviation was 0.05 ml/hr.

REFERENCE 6

A laminated tube consisting of the polyethylene tube and the polyvinylidene tube and having its one end closed was likewise folded in a longitudinal direction, as in Example 8. The laminated tube was subsequently inserted in the vulcanized natural rubber tube in a manner similar to Example 1. The openings of those tubes were then secured one to another, before loading the inside of the inner polyethylene tube with compressed to thereby inflate this composite tube. An excessive end of the treated natural rubber tube was cut and removed from the remainder so that the length of this tube coincided with the polyethylene tube. The end opening of the rubber tube was sealed, and the compressed air was exhausted therefrom. A balloon assembly 'a' prepared in this manner was filled with 60 ml of water through an inlet 4 as shown in FIG. 1, using a syringe. There was observed two large voids and many small voids between the laminated tube and the rubber tube while the balloon was being inflated and expanded by water. Next, the water was allowed to flow into and through the same tube line 'b' as that used in Example 8, and in a manner similar thereto. The water continued to flow out of the balloon at an average dripping rate of 2.3 ml/hr. It took about 24 hours for the balloon to become empty at a standard deviation of 0.42 ml/hr which indicated a much greater variation of flow rate than in Example 8.

In summary, the present invention provides a balloon comprising an elastic rubber layer whose additives will not migrate into the liquid medicine. The time to manufacture the balloons can now be shortened, without involving any problem of allergic reaction or anaphylactic shock which has heretofore been unavoidable in the case of using an untreated elastic rubber.

In a case wherein a liquid lubricant layer is interposed between the outer layer and the impermeable layer, even the balloon whose outer layer shows an expansion stress greater than the inner layer can smoothly expand without producing any partial gaps between, or any stress concentration in either of the layers. Liquid medicine can flow out of the balloon filled therewith in a stable manner such that a noticeable variation will not be caused in the flow rate at the outlet of the balloon, because the pressure of the liquid medicine entering the flow regulator does not significantly vary. Thus, a patient can be dosed with the medicine at a constant flow rate.

What is claimed is:

1. An apparatus for dosing a liquid medicine, the apparatus comprising:

a balloon having first and second openings for receiving an amount of a liquid medicine through said first opening and subsequently delivering it through said second opening;

a delivery assembly connected to and extending from said second opening for regulating the flow of a liquid medicine from the balloon; and a housing in which the balloon is contained and having an outlet for said delivery assembly;

said balloon being composed of an inner layer serving as an inner wall of the balloon, an outer layer disposed outside the inner layer and an impermeable membrane interposed between the inner and outer layers, wherein:

the inner layer is made of a chemically resistant resin not reactive with a liquid medicine, the outer layer is made of an elastic rubber more contractive than the inner layer when the balloon is inflated with a liquid medicine, and the impermeable membrane prevents additives in the elastic rubber from migrating into a liquid medicine.

2. An apparatus as defined in claim 1, wherein the balloon further comprises a liquid lubricant layer interposed between the outer layer and the impermeable membrane.

3. An apparatus as defined in claim 1, wherein the impermeable membrane is formed of at least one thermoplastic resin selected from the group consisting of: polyvinylidene chloride resins, polyvinyl chloride resins, polyamides, thermoplastic polyesters, and ethylenevinyl acetate copolymers.

4. An apparatus as defined in claim 1, wherein the delivery assembly comprises a flow regulator to control said flow.

5. A balloon for dosing a liquid medicine and comprising an inner layer serving as an inner wall of the balloon, an outer layer disposed outside the inner layer and an impermeable membrane interposed between the inner and outer layers, wherein:

the inner layer is made of a chemically resistant resin not reactive with a liquid medicine, the outer layer is made of an elastic rubber more contractive than the inner layer when the balloon is inflated with a liquid medicine, and the impermeable membrane- prevents additives in the elastic rubber from migrating into a liquid medicine.

6. The balloon as defined in claim 5, wherein the balloon further comprises a liquid lubricant layer interposed between the outer layer and the impermeable membrane.

7. The balloon as defined in claim 5, wherein the impermeable membrane is formed of at least one thermoplastic resin selected from the group consisting of: polyvinylidene chloride resins, polyvinyl chloride resins, polyamides, thermoplastic polyesters, and ethylenevinyl acetate copolymers.

8. An apparatus as defined in claim 2, wherein the impermeable membrane is formed of at least one thermoplastic resin selected from the group consisting of: polyvinylidene chloride resins, polyvinyl chloride resins, polyamides, thermoplastic polyesters, and ethylenevinyl acetate copolymers.

9. An apparatus as defined in claim 2, wherein the delivery assembly comprises a flow regulator to control said flow.

10. The balloon as defined in claim 6, wherein the impermeable membrane is formed of at least one thermoplastic resin selected from the group consisting of: polyvinylidene chloride resins, polyvinyl chloride resins, polyamides, thermoplastic polyesters, and ethylenevinyl acetate copolymers.

* * * * *